United States Patent [19]

Fields et al.

[11] Patent Number: 4,851,159
[45] Date of Patent: Jul. 25, 1989

[54] PROCESS FOR THE PREPARATION OF N-PHOSPHONOMETHYLGLYCINE

[75] Inventors: Jr. Fields, Manchester; Raymond C. Grabiak, Maryland Heights; Sherrol L. Baysdon, Chesterfield; Peter E. Rogers, Des Peres, all of Mo.

[73] Assignee: Monsanto Company, St. Louis, Mo.

[21] Appl. No.: 188,930

[22] Filed: May 2, 1988

[51] Int. Cl.⁴ .............................................. C07F 9/38
[52] U.S. Cl. ..................................................... 562/17
[58] Field of Search .................................. 260/502.5 F

[56] References Cited

U.S. PATENT DOCUMENTS

| | | | |
|---|---|---|---|
| 3,779,758 | 3/1974 | Franz | 71/86 |
| 4,369,142 | 1/1983 | Moser | 260/502.5 |
| 4,568,432 | 2/1986 | Rogers | 260/502.5 F |
| 4,670,191 | 6/1987 | Kleiner | 260/502.5 |
| 4,684,483 | 8/1987 | Richard et al. | 260/502.5 F |

FOREIGN PATENT DOCUMENTS 1039739  10/1978  Canada .

OTHER PUBLICATIONS

H. Yanagawa, et al., "Novel Formation of α-Amino Acids and Their Derivatives from Oxo Acids and Ammonia in an Aqueous Medium", *J. Biochem.* 91, 2087–90/1982.

J. Kilberg, "Synthesis of Strombine", *Acta Chemica Scandinavica*, B 37, 911–16, (1983).

*Primary Examiner*—J. E. Evans
*Attorney, Agent, or Firm*—Frank D. Shearin

[57] ABSTRACT

A process is disclosed for the preparation of N-phosphonomethylglycine which comprises bringing together under reaction conditions glyoxylic acid or a derivative thereof and an N-acylaminomethylphosphonic acid represented by the formula

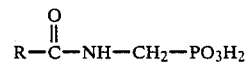

wherein R is selected from the group consisting of alkyl having from one to about 6 carbon atoms, haloalkyl having from one to about six carbon atoms, benzyl and phenyl.

16 Claims, No Drawings

PROCESS FOR THE PREPARATION OF N-PHOSPHONOMETHYLGLYCINE

BACKGROUND OF THE INVENTION

This invention relates to the preparation of N-phosphonomethylglycine, and more particularly to an improved process for producing N-phosphonomethylglycine from an N-acylaminomethylphosphonic acid and glyoxylic acid or derivative without isolation of the N-acylaminomethylphosphonic acid or related intermediates.

N-phosphonomethylglycine is a highly effective and commercially important phytotoxicant useful in controlling the growth of germinating seeds, emerging seedlings, maturing and established woody and herbaceous vegetation, and aquatic plants. The salts of N-phosphonomethylglycine are conveniently applied in an aqueous formulation as a post emergent phytotoxicant or herbicide for the control of a broad spectrum of plant species.

Gaertner, Canadian Patent No. 1,039,739 describes a process for producing N-phosphonomethylglycine by reacting aminomethylphosphonic acid or its esters with glyoxylic acid derivatives to form carbonylaldiminomethanephosphonates. Thereafter, the carbonylaldiminomethanephosphonates are subjected to catalytic hydrogenation to produce N-phosphonomethylglycine or its esters. The ester groups can be hydrolyzed to produce N-phosphonomethylglycine.

Franz, U.S. Pat. No. 3,799,758, describes the preparation of N-phosphonomethylglycine by reacting ethyl glycinate, formaldehyde, and diethyl phosphite followed by hydrolysis. Alternative processes described by Franz include phosphinomethylation of glycine with chloromethylphosphinic acid in the presence of sodium hydroxide and oxidation of N-phosphinomethylglycine with mercuric chloride.

Moser, U.S. Pat. No. 4,369,142, describes a process for the preparation of N-phosphonomethylglycine in which aminomethylphosphonic acid is reacted in aqueous medium with glyoxal in the presence of the catalyst sulfur dioxide.

H. Yanagawa et al., "Novel Formation of α-Amino Acids and Their Derivatives from Oxo Acids and Ammonia in an Aqueous Medium", *J. Biochem*, 91, 2087–2090 (1982) discloses the reaction of glyoxylic acid with ammonia, methylamine, and ammonium sulfate to make glycine and/or its derivatives. On page 2088 in Table I, the synthesis of various amino acids is disclosed at pH 4 and pH 8 and at temperatures of 27° C. and 105° C. At the bottom of the left column bridging to the top of the right column on page 2088, it is disclosed that acidic pH and low temperatures were more favorable than alkaline pH and high temperatures for the formation of glycine.

J. Kihlberg, "Synthesis of Strombine. A · New Method for Monocarboxymethylation of Primary Amines", *Acta Chemica Scandinavica B* 37, 911–916 (1983) discloses the reaction of two equivalents of glyoxylic acid with primary aliphatic and aromatic amines which proceeds via the initial formation of the corresponding imine derivative. In Table I, appearing on page 914, it is disclosed that various starting amines are reacted with 2 equivalents of glyoxylic acid at temperatures between about 25° C. and 70° C. to yield the corresponding N-formyl-N-carboxymethylamine which is easily hydrolyzed to the N-carboxymethylamine.

Kleiner, U.S. Pat. No. 4,670,191 discloses a process for the preparation of N-phosphonomethylglycine by reacting aminomethanephosphonic acid with 2 molar equivalents of glyoxylic acid at temperatures between 10° C. and 100° C.

Although the teachings of the above references, alone or in combination, can be used to produce satisfactory yields of N-phosphonomethylglycine, each of such teachings suffer from one or more disadvantages. Now, there is provided a straightforward process for the production of N-phosphonomethylglycine or its derivatives in good yield with inexpensive raw materials, low capital costs and simple operating procedures, without the necessity of isolating intermediate products.

SUMMARY OF THE INVENTION

These and other advantages are achieved by a process for preparing N-phosphonomethylglycine which comprises bringing together under reaction conditions glyoxylic acid and an N-acylaminomethylphosphonic acid represented by the formula

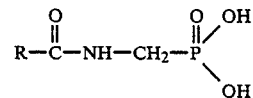

wherein R is selected from the group consisting of alkyl having from 1 to about 6 carbon atoms, haloalkyl having from 1 to about 6 carbon atoms, benzyl and phenyl.

DETAILED DESCRIPTION OF THE INVENTION

The term alkyl as used herein means both straight and branched chain radicals, such as methyl, ethyl, isopropyl, cyclopropyl, cyclohexyl, tertiary butyl, iso-butyl, n-butyl and various forms of phenyl, hexyl and the like. Various alkyl forms containing more than 6 carbon atoms can be used in the process of the present invention, but it does not seem to be particularly advantageous. Methyl is preferred.

The term haloalkyl includes all of the above alkyl groups that have been substituted with one or more halogen atoms, such as chlorine, bromine and iodine. Chloroalkyls are preferred.

The terms benzyl and phenyl have the usual meanings known to those skilled in the art, and such benzyl and phenyl groups can be substituted or unsubstituted. Typical substitutions would include nitro, methyl or halo, such as chloro, but satisfactory results are obtained using the less expensive unsubstituted phenyl groups.

Glyoxylic acid also includes the hydrate, hemiacetal or acetal derivative thereof, or an ester of glyoxylic acid wherein the ester group is an alkyl group having from 1 to 6 carbon atoms, as discussed above. All are good.

The N-acylaminomethylphosphonic acids useful in this process have been reported. In contrast to the report in *Synthesis* (June 1978) pages 479 and 480, it was found that simple alkyl and aryl amides could be phosphonomethylated in good yield on reaction with phosphorus trichloride and formaldehyde, and this is what we prefer to do as the first step in this process.

The molar ratio of glyoxylic acid and N-acylaminomethylphosphonic can affect the yield of N-phosphonomethylglycine. One mole of N- acylaminomethylphosphonic acid to two moles of glyoxylic acid, or more, is preferably used to obtain quantative yields. Molar ratios of less than 1:2 can be used, but the yield of N-phosphonomethylglycine is reduced.

The process of the present invention involves heating the N-acylaminomethylphosphonic acid with glyoxylic acid in water or an aqueous mineral acid to obtain a one pot hydrolysis/reductive alkylation to give N-phosphonomethylglycine. Either a purified N-acylaminomethylphosphonic acid, or crude, stripped oil from the phosphonomethylation reaction can be used with satisfactory results. The use of the crude, unisolated N-acylaminomethylphosphonic acid avoids a costly isolation step, improves the overall yield, reduces waste loads, and this is what we prefer to do.

The temperature of the reaction can vary within wide ranges. Although ambient temperature can be used, the reaction is sluggish, and it is preferred to use temperatures of at least 50° C., and more preferably of at least 70° C. The upper temperature limit of this one pot hydrolysis/reduction alkylation process is only dependent on the hydrolytic stability of the N-acylaminomethylphosphonic acid. Accordingly, the reaction can be run at reflux (about 110° C.) or under pressure at temperatures of about 150° C. From a process standpoint temperatures of about 135° C. to about 140° C. are preferred when using N-benzoylaminomethylphosphonic acid, glyoxylic acid and aqueous hydrochloric acid.

The invention is further illustrated by, but not limited to, the following examples.

EXAMPLE 1

Acetamide to N-Phosphonomethylglycine

A 50 ml flask was charged with acetamide (1.48 g, 0.025 mol), paraformaldehyde (0.79 g, 0.0265 mol) and 7 ml of glacial acetic acid. The mixture was heated to solution ($\sim$100° C.) then cooled to room temperature. Then, phosphorus trichloride (4.11 g, 0.03 mol) was added in one portion, and the temperature rose to 40° C. The solution was heated at 107° C. for 3 hours and then evaporated to an oil at 55° C.

The resulting oil was treated with 5.10 g (0.55 mol) of glyoxylic acid monohydrate in 25 ml water. The solution was heated at reflux overnight. HPLC analysis of the reaction solution showed that it contained a 69.9% yield of N-phosphonomethylglycine and a 7.72% yield of N-formyl-N-phosphonomethylglycine.

EXAMPLE 2

Acetamide to N-Phosphonomethylglycine with Glyoxylic Acid Methylester Methylhemiacetal as the Reductive Agent Acetamide (2.96 g, 0.05 mol) was phosphonomethylated as described in Example 1. After heating at 107° C. for 3 hours, methyl 2-hydroxy-2-methoxy acetate and 5 ml of H$_2$O was introduced and the reaction solution was evaporated to a thick oil. The oil was treated with 50 ml of concentrated HCl and heated at reflux overnight.

Ion exchange purification of the reaction mixture gave 6.2 g of N-phosphonomethylglycine which represents a 73.4% yield based on acetamide.

EXAMPLE 3

Benzamide to N-Phosphonomethylglycine

A 100 ml flask was charged with benzamide (3.02 g, 0.025 mol), paraformaldehyde (0.79 g, 0.0265 mol) and 20 ml of glacial acetic acid. The mixture was heated to solution ($\sim$100° C.) and cooled to 10° C. in an ice bath. Phosphorus trichloride (3.6 g, 0.0265 mol) was added dropwise keeping the temperature below 30° C. The solution was heated to 120° C. over a one-hour period and held at 120° C. for 2 hours. After heating, the solution was evaporated at reduced pressure to remove the acetic acid and obtain the N-benzoylaminomethylphosphonic acid as an oil.

The oil was treated with gloxylic acid monohydrate (4.85 g, 0.053 mol) and 25 ml of concentrated HCl and heated at reflux for 8 hours. HPLC analysis of the resulting solution showed the presence of an 82.4% yield of N-phosphonomethylglycine based on benzamide.

EXAMPLE 4

Benzamide Using a High Temperature/Pressure Reductive Alkylation Step

Benzamide (6.1 g, 0.05 mol) was phosphonomethylated as described in Example 3. After evaporation of acetic acid, the oil was transferred to a 250 ml Fisher-Porter bottle equipped with a pressure gauge and pressure release valve. The oil was treated with glyoxylic acid monohydrate (10.4 g, 0.11 mol) in 30 ml of concentrated HCl (aq). The mixture was pressurized to $2.07 \times 10^5 N/m^2$ (30 psi) with nitrogen and heated in an oil bath to an oil temperature between 130°–138° C. Pressure was released periodically to maintain an internal pressure between $2.90 \times 10^5$ to $3.58 \times 10^5 N/m^2$ (42–52 psi). After 3.5 hours, gas evolution ceased and the reaction was cooled.

HPLC analysis of the reaction mixture revealed an 82.5% yield of N-phosphonomethylglycine and a 4.5% yield of N-formyl-N-phosphonomethylglycine based on benzamide.

EXAMPLE 5

Phenyl Carbamate to N-Phosphonomethylglycine

A 50 ml flask was charged with phenyl carbamate (3.53 g) formaldehyde (0.79 g) and acetic acid (20 ml). The mixture was heated to 85° C. and then cooled to about 15° C. in an ice bath. Phosphorous trichloride (4.11 g) was added in one portion and the solution was heated to 107° C. over a one hour period. After heating at 107° C. for 2.5 hours and stirring at room temperature overnight, the solution was stripped to an oil.

The oil was heated with glyoxylic acid monohydrate (5.1 g) in 25 ml of H$_2$O and heated at reflux for 12 hours. Analysis of the reaction mixture by HPLC showed the presence of N-phosphonomethylglycine (21.6% yield) N,N-iminomethylphosphonic acid (15.9% yield) and iminodiacetic acid (25.9% yield).

EXAMPLE 6

N-Chloroacetylaminomethylphosphonic Acid to N-Phosphonomethylglycine

A 50 ml flask was charged with N-chloroacetylaminomethylphosphonic acid (0.2 g, 0.001 mole) and glyoxylic acid (0.22 g, 0.002 mole) and 2 ml of water. The mixture was heated at reflux for 12 hours. Analysis of the resulting solution by HPLC showed the presence of N-phosphonomethylglycine (76.8% yield), N-formyl-N-phosphonomethylglycine (5.6% yield) and aminomethylphosphonic acid (3.5% yield).

Although the invention has been described in terms of specified embodiments which are set forth in considerable detail, it should be understood that this is by way of illustration only, and that alternative embodiments and operating techniques will become apparent to those skilled in the art in view of the disclosure. For example, when the N-acylaminomethylphosphonic acid is brought together with glyoxylic acid in the presence of hydrochloric acid, the acyl substituent is converted into the corresponding carboxylic acid, which can be recovered and used to prepare the amide starting material useful in this process. As another example, other derivatives of glyoxylic acid, such as esters other than alkyl, can be used in the process of the present invention.

Accordingly, modifications can be made without departing from the spirit of the described invention.

What is claimed is:

1. A process for the preparation of N-phosphonomethylglycine which comprises bringing together under reaction conditions a glyoxylic compound which is glyoxylic acid, hydrate, hemiacetal, acetal or alkyl ester thereof and an N-acylaminomethylphosphonic acid represented by the formula

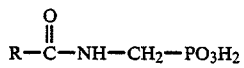

wherein R is selected from the group consisting of alkyl having from one to about 6 carbon atoms, haloalkyl having from one to about six carbon atoms, benzyl and phenyl.

2. A process of claim 1 wherein the mole ratio of glyoxylic compound to N-acylaminomethylphosphonic acid is at least 2:1.

3. A process of claim 1 wherein the N-acylaminomethylphosphonic acid and the glyoxylic compound thereof are brought together and heated to a temperature between about 50° C. and about 180° C.

4. A process of claim 3 wherein the temperature is between about 70° C. and about 150° C.

5. A process of claim 1 wherein R is alkyl.

6. A process of claim 5 wherein R is methyl.

7. A process of claim 1 wherein R is phenyl.

8. A process for the preparation of N-phosphonomethylglycine which comprises bringing together in the presence of water or an aqueous a mineral acid and at a temperature between about 70° C. and about 150° C. a glyoxylic compound which is glyoxylic acid, hydrate, hemiacetal, acetal or alkyl ester thereof and an N-acylaminomethylphosphonic acid represented by the formula

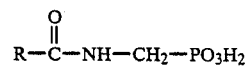

wherein R is selected from the group consisting of alkyl having from one to about 6 carbon atoms, and phenyl wherein the mole ratio of glyoxylic acid to N-acylaminomethylglyphosphonic acid is at least 2:1.

9. A process of claim 8 wherein the mineral acid is hydrochloric acid or sulfuric acid.

10. A process of claim 8 wherein R is phenyl.

11. A process of claim 10 wherein the mineral acid is hydrochloric acid.

12. A process of claim 8 wherein R is methyl.

13. A process of claim 12 wherein water without added mineral acid is used.

14. A process of claim 8 wherein the glyoxylic compound is the alkyl ester of glyoxylic acid, wherein the alkyl group contains from one to about six carbon atoms.

15. A process of claim 8 wherein the glyoxylic compound is the alkyl ester hemiacetal of glyoxylic acid, wherein the alkyl group contains from one to about six carbon atoms.

16. A process of claim 1 wherein the N-acylaminomethylphosphonic acid is prepared by bringing together under substantially anhydrous reaction conditions an amide represented by the formula

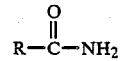

wherein R is as defined above, paraformaldehyde, and phosphorus trichloride, and without isolation of the N-acylaminomethylphosphonic acid, adding glyoxylic compound to the reaction mixture.

* * * * *